United States Patent [19]

Koppe et al.

[11] 3,959,338

[45] May 25, 1976

[54] 1-(CYANO-PHENOXY)-2-HYDROXY-3-HYDROXYALKYLAMINO-PROPANES AND SALTS THEREOF

[75] Inventors: Herbert Koppe; Helmut Stahle; Werner Kummer, all of Ingelheim am Rhein; Werner Traunecker, Munster-Sarmsheim, all of Germany

[73] Assignee: Boehringer Ingelheim GmbH, Ingelheim am Rhein

[22] Filed: Mar. 18, 1974

[21] Appl. No.: 451,820

Related U.S. Application Data

[63] Continuation-in-part of Ser. No. 185,897, Oct. 1, 1971, abandoned.

[30] Foreign Application Priority Data

Oct. 5, 1970 Germany............................. 2048838

[52] U.S. Cl.............................. 260/465 E; 424/304
[51] Int. Cl.².................................... C07C 121/80
[58] Field of Search .................................. 260/465 E

[56] References Cited
UNITED STATES PATENTS 3,541,130  11/1970  Koppe et al. ........................ 260/465
3,663,607  5/1972  Barrett et al..................... 260/465 X

*Primary Examiner*—Lewis Gotts
*Assistant Examiner*—Dolph H. Torrence
*Attorney, Agent, or Firm*—Hammond & Littell

[57] ABSTRACT

Racemic or optically active compounds of the formula

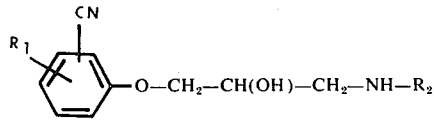

wherein
$R_1$ is hydrogen, halogen, alkyl or 1 to 4 carbon atoms or alkoxy of 1 to 4 carbon atoms, and
$R_2$ is straight or branched hydroxyalkyl of 3 to 6 carbon atoms, and non-toxic, pharmacologically acceptable acid addition salts thereof; the compounds as well as the salts are useful β-adrenergic receptor blocking agents and hypotensives.

5 Claims, No Drawings

1-(CYANO-PHENOXY)-2-HYDROXY-3-HYDROXYALKYLAMINO-PROPANES AND SALTS THEREOF

This is a continuation-in-part of copending application Ser. No. 185,897, filed October 1, 1971 now abandoned.

This invention relates to novel 1-(cyano-phenoxy)-2-hydroxy-3-hydroxyalkylamino-propanes and non-toxic acid addition salts thereof, as well as to various methods of preparing these compounds.

More particularly, the present invention relates to racemic or optically active compounds of the formula

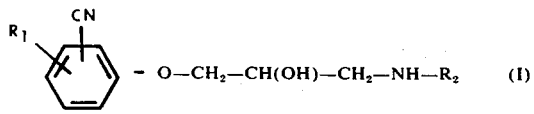

wherein
$R_1$ is hydrogen, halogen, alkyl of 1 to 4 carbon atoms or alkoxy of 1 to 4 carbon atoms, and
$R_2$ is straight or branched hydroxyalkyl of 3 to 6 carbon atoms,
and non-toxic, pharmacologically acceptable acid-addition salts thereof.

The compounds embraced by formula I above may be prepared by a number of different methods, among which the following have proved to be particularly convenient and efficient:

Method A

By reacting a compound of the formula

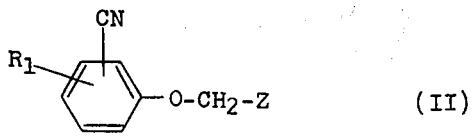

wherein $R_1$ has the same meaning as in formula I and Z is

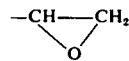

or —CH(OH)—CH$_2$—Hal, where Hal is halogen, with a hydroxyalkylamine of the formula

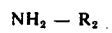      (III)

wherein $R_2$ has the same meaning as in formula I.

Method B

For the preparation of a compound of the formula I wherein $R_1$ is halogen, by introducing a halogen substituent into a compound of the formula

wherein $R_2$ has the same meanings as in formula I and Ar is

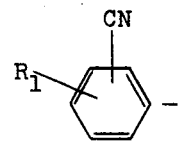

The halogenation may, for example, be effected by reacting the compound (IV) with a mixture consisting of concentrated hydrogen peroxide and the corresponding hydrohalic acid at elevated temperatures, provided the starting compound does not contain a grouping which is altered by the said reagent mixture.

Some of the starting compounds needed for methods A and B are known compounds, and the remainder may be prepared by conventional, known processes.

Thus, the epoxides of the formula II may readily be prepared by reacting ethylene oxide with a corresponding phenol or phenolate of the formula

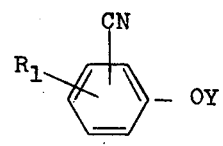

(V)

wherein $R_1$ has the same meanings as in formula I and Y is hydrogen or a cation, such as an alkali metal cation.

The epoxides of the formula II may, in turn, be used for the preparation of other starting compounds; for instance, the halohydrins of the formula II may be prepared by reacting an epoxide of the formula II with the corresponding hydrohalic acid.

The amines embraced by formula III are known compounds, the majority of them being commercial products.

The compounds of the formulas IV and V which already contain the 1-(cyano-phenoxy)-2-hydroxy-3-hydroxyalkylamino-propane structure, may be prepared in a manner analogous to that described in method A above, that is, starting from the corresponding phenol, by reacting the same with epichlorohydrin to form the corresponding intermediate 1-(cyano-phenoxy)-2,3-epoxypropane, and reacting the latter with a hydroxyalkylamine of the formula III.

The compounds embraced by formula I comprise an asymmetric carbon atom in the —CH(OH)-group and therefore occur in the form of racemic mixtures as well as optical antipodes. The latter may be obtained either from the racemic mixtures by fractional precipitation with the aid of conventional optically active auxiliary acids, such as dibenzoyl- or di-p-toluyl-D-tartaric acid or D-3-bromo-camphor-8-sulfonic acid, or by starting from the corresponding optically active starting material.

The end products of the formula I are organic bases and therefore form acid addition salts with inorganic or organic acids. Examples of non-toxic, pharmacologically acceptable acid addition salts are those formed with hydrochloric acid, hydrobromic acid, sulfuric acid, methanesulfonic acid, maleic acid, acetic acid, oxalic acid, lactic acid, tartaric acid, 8-chlorotheophylline or the like.

The compounds of the formula I are capable of ester formation with carboxylic acids. Such esters may be obtained in conventional fashion, such as by reacting a compound of the formula I with a carboxylic acid halide or a carboxylic acid anhydride. Examples of preferred esters are the 2-acetates or 2-propionates.

The following examples further illustrate the present invention and will enable others skilled in the art to understand it more completely. It should be understood, however, that the invention is not limited solely to the particular examples given below.

EXAMPLE 1

1-(2'-Cyano-phenoxy)-2-hydroxy-3-[(1'',1''-dimethyl-2''-hydroxyethyl)-amino]-propane and its hydrochloride by method A 17.5 gm (0.1 mol) of 1-(2'-cyano-phenoxy)-2,3-epoxy-propane and 8.9 gm (0.1 mol) of 2-amino-2-methyl-propanol-1 were dissolved in 100 ml of ethanol, and the solution was refluxed for 2 hours. Thereafter, the ethanol was distilled off, and the residue was admixed with dilute hydrochloric acid. The insoluble components were filtered off, the filtrate was made alkaline with aqueous 20% sodium hydroxide, the precipitate formed thereby was taken up in chloroform, and the chloroformic solution was washed with water, dried and evaporated. The residue was recrystallized twice from ethyl acetate, yielding the pure free base 1-(2'-cyano-phenoxy)-2-hydroxy-3-[(1'',1''-dimethyl-2''-hydroxy-ethyl)-amino]-propane.

The free base was dissolved in ethanol, and the resulting solution was acidified with ethereal hydrochloric acid, whereby 9.5 gm of the hydrochloride, m.p. 132°–134°C, of the formula

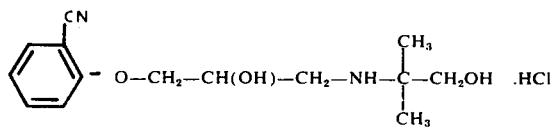

precipitated out.

EXAMPLE 2

1-(2'-Cyano-phenoxy)-2-hydroxy-3-[(1''-ethyl-2''-hydroxyethyl)-amino]-propane and its hydrochloride by method A 17.5 gm (0.1 mol) of 1-(2'-cyano-phenoxy)-2,3-epoxy-propane and 13.3 gm (0.15 mol) of 2-amino-butanol-1 were dissolved in 100 ml of ethanol, and the solution was refluxed for two hours. Thereafter, the ethanol was distilled off, the residue was admixed with dilute hydrochloric acid, and the acidic mixture was filtered to remove insoluble components. The filtrate was made alkaline with aqueous 20% sodium hydroxide, and the crystalline precipitate formed thereby was collected by vacuum filtration and recrystallized from ethyl acetate, yielding the pure free base 1-(2'-cyano-phenoxy)-2-hydroxy-3-[(1''-ethyl-2''-hydroxy-ethyl)-amino]-propane.

The free base was dissolved in acetonitrile, and the solution was acidified with ethereal hydrochloric acid, whereby 6.1 gm of the hydrochloride, m.p. 106°–108°C, of the formula

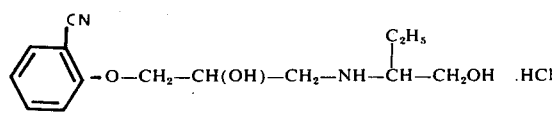

precipitated out.

EXAMPLE 3

1-(2'-Cyano-5'-methyl-phenoxy)-2-hydroxy-3-[(1'',1''-dimethyl-2''-hydroxy-ethyl)-amino]-propane and its hydrochloride by method A 7.55 gm (0.04 mol) of 1-(2'-cyano-5'-methyl-phenoxy)-2,3-epoxy-propane and 7.1 gm (0.08 mol) of 2-amino-2-methylpropanol-1 were dissolved in 70 ml of ethanol, and the solution was refluxed for 2 hours. Thereafter, the ethanol was distilled off, and the residue, raw 1-(2'-cyano-5'-methylphenoxy)-2-hydroxy-3-[(1'',1''-dimethyl-2''-hydroxy-ethyl)-amino]-propane, was admixed with ether and dilute hydrochloric acid. The crystalline substance formed thereby was collected by vacuum filtration and recrystallized from ethanol and ether, yielding 4.5 gm of the hydrochloride, m.p. 193° – 196°C, of the formula

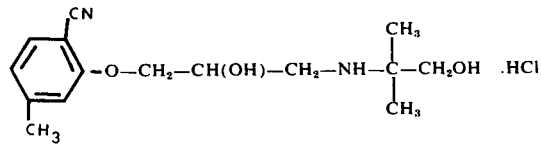

EXAMPLE 4

Using a procedure analogous to that described in Example 1, 1-(2'-cyano-phenoxy)-2-hydroxy-3-[(2''-hydroxy-n-propyl)-amino]-propane and its hydrochloride, m.p. 112°–116°C, of the formula

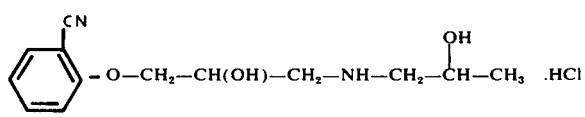

were prepared from 1-(2'-cyano-phenoxy)-2,3-epoxy-propane and (2-hydroxy-n-propyl)-amine.

EXAMPLE 5

Using a procedure analogous to that described in Example 1, 1-(2'-cyano-5'-methyl-phenoxy)-2-hydroxy-3-[(2''-hydroxy-n-propyl)-amino]-propane and its hydrochloride, m.p. 143°–147°C, of the formula

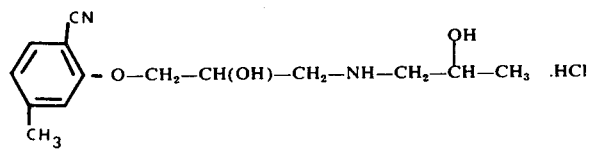

were prepared from 1-(2'-cyano-5'-methyl-phenoxy)-2,3-epoxypropane and (2-hydroxy-n-propyl)-amine.

EXAMPLE 6

1-(2'-Cyano-phenoxy)-2-hydroxy-3-[(2''-methyl-2''-hydroxyethyl)-amino]-propane and its hydrochloride by method A A mixture consisting of 0.3 gm (about 0.0015 mol) of 1-(2'-cyano-phenoxy)-2-hydroxy-3-amino-propane, 5 ml of absolute ethanol, 0.21 gm (0.002 mol) of sodium carbonate, 30 mgm of potassium iodide and 0.189 gm (0.002 mol) of propylene chlorohydrin was refluxed for 20 hours, accompanied by stirring. Thereafter, the reaction mixture was worked up in conventional manner, and the isolated raw reaction product was purified by chromatography in a silicagel column, yielding the free base 1-(2'-cyano-phenoxy)-2-hydroxy-3-[(2''-methyl-2''-hydroxy-ethyl)-amino]-propane.

The free base was dissolved in ethanol, and the resulting solution was acidified with ethereal hydrochloric acid, whereby the hydrochloride, m.p. 108/109°–111°C, of the formula

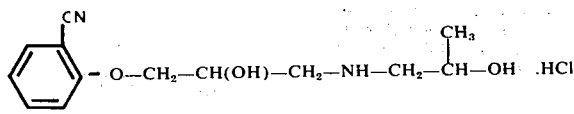

precipitated out.

EXAMPLE 7

1-(2'-Cyano-4'-chloro-phenoxy)-2-hydroxy-3-[(1'',-1''-dimethyl-2''-hydroxy-ethyl)-amino]-propane by method B 9.7 gm (about 0.037 mol) of 1-(2'-cyano-phenoxy)-2-hydroxy-3-[(1'',1''-dimethyl-2''-hydroxy-ethyl)-amino]-propane, prepared as in Example 1, were dissolved in 75 ml of concentrated hydrochloric acid, the solution was heated to 45°C., and then 4.7 gm of an aqueous 30% hydrogen peroxide solution (about 0.038 H₂O₂) were added dropwise. A strong exothermic reaction ensued, and the temperature of the reaction mixture was kept at 65°C. by exterior cooling. After all of the peroxide had been added, the reaction solution was stirred for 30 minutes at 60°–65°C. and subsequently evaporated to dryness in vacuo. The residue was dissolved in water, the resulting solution was extracted twice with ether, and the aqueous phase was made alkaline with 2N sodium hydroxide. The oily precipitate formed thereby was taken up in ether, and the resulting solution was washed with water, dried and evaporated, leaving 9.3 gm of a solid residue which was recrystallized twice from ethyl acetate by addition of petroleum ether (40°–60°C.). 6.6 gm of the compound of the formula

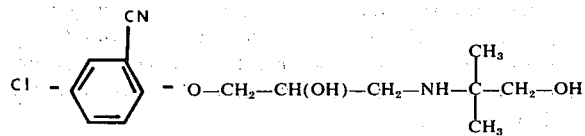

having a melting point of 102°–103°C. were obtained.

EXAMPLE 8

1-(2'-Methoxy-4'-cyano-phenoxy)-2-hydroxy-3-[(1''-methyl-2''-hydroxy-ethyl)-amino]-propane and its hydrochloride by method A 10 gm (0.05 mol) of 1-(2'-methoxy-4'-cyanophenoxy)-2,3-epoxy-propane were dissolved in 150 ml of ethanol, 4 gm of 2-amino-propanol-1 were added to the solution, and the resulting mixture was refluxed for 2 hours. Thereafter, the ethanol was distilled off, the residue was admixed with water, the aqueous mixture was acidified with dilute hydrochloric acid, and the insoluble components were filtered off. The filtrate was alkaline with aqueous 20% sodium hydroxide and then extracted three times with ethyl acetate. The combined organic extracts were washed with water, dried and evaporated, leaving as a crystalline residue the raw free base 1-(2'-methoxy-4'-cyano-phenoxy)-2-hydroxy-3-[(1''-methyl-2''-hydroxy-ethyl)-amino]-propane.

The free base was dissolved in ethanol, the resulting solution was acidified with ethanolic hydrochloric acid, ether was added to the acidic solution, and the precipitate formed thereby was collected and recrystallized three times more from ethanol by addition of ether, yielding 2.1 gm of the hydrochloride, m.p. 147°C., of the formula

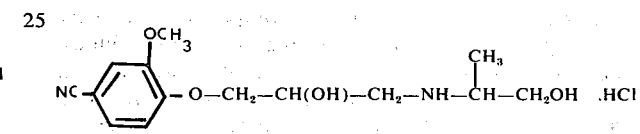

EXAMPLE 9

Using a procedure analogous to that described in Example 8, 1-(2'-methoxy-4'2-hydroxy-3-[(1'',1''-dimethyl-2''-hydroxy-ethyl)-amino]-propane and its hydrochloride, m.p. 128°–129°C., of the formula

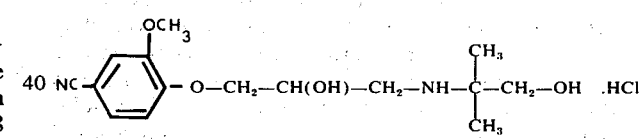

were prepared from 1-(2''-methoxy-4'-cyano-phenoxy)-2,3-epoxy-propane and 2-amino-2-methyl-propanol-1.

EXAMPLE 10

Using a procedure analogous to that described in Example 7, 1-(2'-cyano-4'-chloro-phenoxy)-2-hydroxy-3-[(1''-methyl-2''-hydroxy-ethyl)-amino]-propane, of the formula

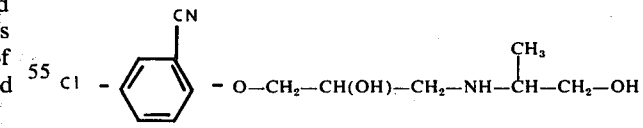

was prepared from 1-(2'-cyano-phenoxy)-2-hydroxy-3-[(1''-methyl-2''-hydroxy-ethyl)-amino]-propane. The compound exists in two stereoisomeric forms which may be separated by fractional crystallization, one of the stereoisomers melting at 141° – 143°, the other at 113° – 114°C.

The compounds according to the present invention, that is, the racemates or optical antipodes of those embraced by formula I above, esters thereof and non-toxic, pharmacologically acceptable acid addition salts thereof, have useful pharmacodynamic properties.

More particularly, the compounds of the instant invention exhibit β-adrenergic receptor blocking activity in warm-blooded animals, such as guinea pigs, and are therefore useful for the treatment and prophylaxis of disorders of the coronary vessels of the heart and for the treatment of cardiac arrhythmias, especially tachycardia. In addition, the compounds of the invention exhibit hypotensive activity. In comparison to known β-adrenergic receptor blocking agents, such as 1(1'-naphthyloxy)-2-hydroxy-3-isopropylamino-propane, the compounds of the present invention have the advantage of considerably reduced toxicity.

Within the class of compounds defined by formula I, those wherein $R_4$ is branched hydroxyalkyl, and particularly 1,1-dimethyl-2-hydroxy-ethyl, are especially effective β-adrenergic receptor blocking agents.

Moreover, compounds of the formula I wherein $R_1$ is preferably hydrogen or also alkyl and wherein the cyano substituent is particularly in the 2-position of the phenoxy moiety, exhibit an especially favorable activity spectrum. Specific examples of this subgeneric class are 1-(2'-cyanophenoxy)-2-hydroxy-3-[(1'',1''-dimethyl-2''-hydroxy-ethyl)-amino]-propane, esters thereof, and non-toxic acid addition salts thereof.

Another subgeneric class of compounds which exhibit especially effective β-adrenergic receptor blocking activities are those of the formula I wherein the cyano substituent is in the 2-position on the phenoxy moiety and $R_1$ is 5-lower alkyl, preferably 5-methyl. Specific examples of this subgenus are 1-(2'-cyano-5'-methyl-phenoxy)-2-hydroxy-3-[(1'',1''-dimethyl-2''-hydroxy-ethyl)-amino]-propane, esters thereof, and non-toxic acid addition salts thereof.

For pharmaceutical purposes the compounds according to the present invention are administered to warm-blooded animals perorally or parenterally as active ingredients in customary dosage unit compositions, that is, compoisitins in dosage unit form consisting essentially of an inert pharmaceutical carrier and one effective dosage unit of the active ingredient, such as tablets, coated pills, capsules, wafers, powders, solutions, suspensions, emulsions, syrups, suppositories and the like. One effective dosage unit of the compounds according to the present invention is from 0.0166 to 5.0 mgm/kg body weight, preferably 0.083 to 1.67 mgm/kg body weight (oral) or 0.0166 to 0.34 mgm/kg body weight (parenteral).

The following examples illustrate a few dosage unit compositions comprising a compound of the present invention as an active ingredient and represent the best modes contemplated of putting the invention into practical use. The parts are parts by weight unless otherwise specified.

EXAMPLE 11

Tablets

The tablet composition is compounded from the following ingredients:

| | |
|---|---|
| 1-(2'-Cyano-phenoxy)-2-hydroxy-3-[(1'',1''-dimethyl-2''-hydroxy-ethyl)-amino]-propane . HCl | 40.0 parts |
| Corn starch | 164.0 parts |
| Secondary calcium phosphate | 240.0 parts |
| Magnesium stearate | 1.0 parts |
| Total | 445.0 parts |

Preparation

The individual ingredients are intimately admixed with each other, the mixture is granulated in conventional fashion, and the granulate is compressed into 445 mgm-tablets in a conventional tablet making machine. Each tablet contains 40 mgm of the phenoxy-amino-propane compound and is an oral dosage unit composition with effective β-adrenergic receptor blocking action.

The same results are obtained when an equal amount of 1-(2'-cyano-phenoxy)-2-hydroxy-3-[(1'''-ethyl-2''-hydroxyethyl)-amino]-propane. HCl or 1-(2'-cyanophenoxy)-2-hydroxy-3-[(2''-methyl-2''-hydroxyethyl)-amino]-propane . HCl is substituted for the particular phenoxy-amino-propane salts in the above tablet composition.

EXAMPLE 12

Gelatin Capsules

The capsule filler composition is compounded from the following ingredients:

| | |
|---|---|
| 1-(2'-Cyano-phenoxy)-2-hydroxy-3-[(1'',1''-dimethyl-2''-hydroxy-ethyl)-amino]-propane . HCl | 25.0 parts |
| Corn starch | 175.0 parts |
| Total | 200.0 parts |

Preparation

The ingredients are intimately admixed with each other, and 200 mgm-portions of the mixture are filled into gelatin capsules of suitable size. Each capsule contains 25 mgm of the phenoxy-amino-propane compound and is an oral dosage unit composition with effective β-adrenergic receptor blocking action.

EXAMPLE 13

Hypodermic Solution

The solution is compounded from the following ingredients:

| | |
|---|---|
| 1-(2'-Cyano-5'-methyl-phenoxy)-2-hydroxy-3-[(1'',1''-dimethyl-2''-hydroxy-ethyl)-amino]-propane . HCl | 2.5 parts |
| Sodium salt of EDTA | 0.2 parts |
| Distilled water q.s.ad | 100.0 parts |

Preparation

The phenoxy-amino-propane compound and the EDTA salt are dissolved in a sufficient amount of distilled water, the solution is diluted to the desired volume with additional distilled water and then filtered until free from suspended particles, and the filtrate is filled under aseptic conditions into 1cc-ampules, which are then sterilized and sealed. Each ampule contains 25 mgm of the phenoxy-amino-propane compound, and the contents thereof are an injectable dosage unit composition with effective β-adrenergic receptor blocking action.

The same result is obtained when an equal amount of 1-(2'-cyano-5'-methyl-phenoxy)-2-hydroxy-3-[(2''-hydroxy-n-propyl)-amino]-propane. HCl is substituted for the phenoxy-amino-propane salt in the above hypodermic solution.

EXAMPLE 14

Sustained Release Pills

The pill core composition is compounded from the following ingredients:

| | |
|---|---|
| 1-(2'-Cyano-phenoxy)-2-hydroxy-3-[(1'',1''-dimethyl-2''-hydroxy-ethyl)-amino]-propane . HCl | 25.0 parts |
| Carboxymethyl cellulose (CMC) | 295.0 parts |
| Stearic acid | 20.0 parts |
| Cellulose acetate phthalate (CAP) | 40.0 parts |
| Total | 380.0 parts |

Preparation

The phenoxy-amino-propane compound, the CMC and the stearic acid are intimately admixed with each other, and the mixture is granulated in conventional manner using a solution of the CAP in 200 ml of a mixture of equal parts of ethanol and ethyl acetate. The granulate is compressed into 380 mgm-pill cores, which are then coated in conventional manner with a sugar-containing aqueous 5% solution of polyvinylpyrrolidone. Each coated pill contains 25 mgm of the phenoxy-amino-propane compound and is an oral dosage unit composition with effective β-adrenergic receptor blocking action.

A dosage unit composition containing a compound of the present invention as an active ingredient may, in addition, also comprise an effective dosage unit of one or more other active ingredients having the same or different pharmacodynamic properties, such as coronary dilators, sympathicomimetics, cardiac glycosides or tranquilizers, as illustrated by the following exazmle:

EXAMPLE 15

Tablets

The tablet composition is compounded from the following ingredients:

| | |
|---|---|
| 1-(2'-Cyano-phenoxy)-2-hydroxy-3-[(1'',1''-dimethyl-2''-hydroxy-ethyl)-amino]-propane . HCl | 35.0 parts |
| 2,6-Bis-(diethanolamino)-4,8-dipiperidino-pyrimido[5,4-d]pyrimidine | 75.0 parts |
| Lactose | 164.0 parts |
| Corn starch | 194.0 parts |
| Colloidal silicic acid | 14.0 parts |
| Polyvinylpyrrolidone | 6.0 parts |
| Magnesium stearate | 2.0 parts |
| Soluble starch | 10.0 parts |
| Total | 500.0 parts |

Preparation

The phenoxy-amino-propane compound, the pyrimidopyrimidine compound, the lactose, the corn starch, the silicic acid and the polyvinylpyrrolidone are intimately admixed with each other, the mixture is granulated in conventional manner using an aqueous solution of the soluble starch, the granulate is admixed with the magnesium stearate, and the finished composition is compressed into 500 mgm-tablets in a conventional tablet making machine. Each tablet contains 35 mgm of the phenoxy-amino-propane compound and 75 gm of the pyrimidopyrimidine compound and is an oral dosage unit composition with effective β-adrenergic receptor blocking and coronary vasodilating actions.

Analogous results are obtained when any one of the other compounds embraced by formula I or a non-toxic acid addition salt thereof is substituted for the particular phenoxy-amino-propane in Examples 11 through 15. Likewise, the amount of active ingredient in these illustrative examples may be varied to achieve the dosage unit range set forth above, and the amounts and nature of the inert pharmaceutical carrier ingredients may be varied to meet particular requirements.

While the present invention has been illustrated with the aid of certain specific embodiments thereof, it will, be readily apparent to others skilled in the art that the invention is not limited to these particular embodiments, and that various changes and modifications may be made without departing from the spirit of the invention or the scope of the appended claims.

We claim:

1. A racemic or optically active compound of the formula

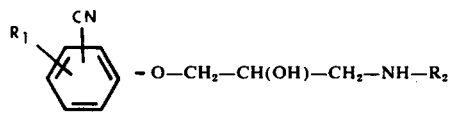

wherein
$R_1$ is hydrogen, chlorine, alkyl of 1 to 4 carbon atoms or alkoxy of 1 to 4 carbon atoms or alkoxy of 1 to 4 carbon atoms, and
$R_2$ is straight or branched monohydroxyalkyl of 3 to 4 carbon atoms, or a non-toxic, pharmacologically acceptable acid addition salt thereof.

2. A compound of claim 1, wherein $R_1$ is hydrogen or alkyl of 1 to 4 carbon atoms, and $R_2$ is branched monohydroxyalkyl of 3 to 4 carbon atoms.

3. A compound of claim 1, wherein $R_1$ is hydrogen or methyl, and $R_2$ is branched monohydroxyalkyl of 3 to 4 carbon atoms.

4. A compound according to claim 1, which is 1-(2'-cyano-phenoxy)-2-hydroxy-3-[(1'',1''-dimethyl-2''-hydroxy-ethyl)-amino]-propane or a non-toxic, pharmacologically acceptable acid addition salt thereof.

5. A compound according to claim 1, which is 1-(2'-cyano-5'-methyl-phenoxy)-2-hydroxy-3-[(1'',1''-dimethyl-2''-hydroxy-ethyl)-amino]-propane or a non-toxic, pharmacologically acceptable acid addition salt thereof.

* * * * *

UNITED STATES PATENT OFFICE
CERTIFICATE OF CORRECTION

Patent No. 3,959,338  Dated May 25, 1976

Inventor(s) HERBERT KOPPE, HELMUT STAHLE, WERNER KUMMER and WERNER TRAUNECKER

It is certified that error appears in the above-identified patent and that said Letters Patent are hereby corrected as shown below:

In Col. 6, line 34  After "4'" and before "2-hydroxy" insert -- -cyano-phenoxy)- --

Signed and Sealed this

Seventeenth Day of August 1976

[SEAL]

Attest:

RUTH C. MASON
Attesting Officer

C. MARSHALL DANN
Commissioner of Patents and Trademarks